(12) United States Patent
Marshall

(10) Patent No.: US 6,589,771 B1
(45) Date of Patent: Jul. 8, 2003

(54) METHODS FOR AROUSING DORMANT BACTERIA

(75) Inventor: William E. Marshall, Bedford Hills, NY (US)

(73) Assignee: Immunom Technologies, Inc., Bedford Hills, NY (US)

( * ) Notice: Subject to any disclaimer, the term of this patent is extended or adjusted under 35 U.S.C. 154(b) by 0 days.

(21) Appl. No.: 09/429,199

(22) Filed: Oct. 28, 1999

(51) Int. Cl.$^7$ .............................. C12N 1/00; C12N 1/04; C12N 1/20; C12N 1/36; C12N 1/38
(52) U.S. Cl. ....................... 435/243; 435/244; 435/245; 435/252.4; 435/252.8; 435/252.9; 435/260; 435/849; 435/856; 435/857; 435/875
(58) Field of Search .............................. 435/243, 252.1, 435/244, 260, FOR 123

(56) References Cited

U.S. PATENT DOCUMENTS 5,314,542 A * 5/1994 Cassidy et al. ............. 119/231

FOREIGN PATENT DOCUMENTS

WO     WO 97/34996     9/1997

OTHER PUBLICATIONS

Wood, Janet M., Osmosensing by Bacteria: Signals and Membrane–Based Sensors, *Microbiology and Molecular Biology Reviews*, 1999, vol. 63, No. 1, p. 230–262.

Yan Min Hu, et al., Protein synthesis is shutdown in dormant *Mycobacterium tuberculosis* and is reversed by oxygen or heat shock, *Federation of European Microbiological Societies*, 1998, FEMS Microbiology Letters 158, p. 139–145.

Mukamolova, Galina V., et al., A bacterial cytokine, *Proc. Natl. Acad. Sci. USA, 1998*, vol. 95, p. 8916–8921.

Steinert, Michael, et al., Resuscitation of Viable but Non-culturable *Legionella pneumophia* Philadelphia JR32 by *Acanthamoeba castellanii*, *Applied and Environmental Microbiology*, 1997, vol. 63, No. 5, p. 2047–2053.

Barer, M.R. (Editorial), Viable but non–culturable and dormant bacteria: time to resolve an oxymoron and a misnomer?, *J. Med. Microbiol*, 1997, vol. 46 p. 629–631.

Weichart, Dieter, et al., Stress resistance and recovery potential of culturable and viable but nonculturable cells of *Vibrio vulnificus*, *Microbiology*, 1996, vol. 142, p. 845–853.

Rahman, Ishrat, et al., Methionine Uptake and Cytopathogenicity of Viable but Nonculturable *Shiegella dysenteriae* Type 1, *Applied and Environmental Microbiology*, 1994, vol. 60, No. 10, p. 3573–3578.

Kaprelyants, Arseny S., et al., Estimation of dormant *Micrococcus luteus* cells by penicillin lysis and by resuscitation in cell–free spent culture medium at high dilution, *Federation of European Microbiological Societies*, 1994, FEMS Microbiology Letters 115, p. 347–352.

Peters, Albert J., D.O., et al., Salpingitis or Oophoritis: What Causes Fever Following Oocyte Aspiration and Embryo Transfer?, *Obstetrics & Gynecology*, 1993, vol 81, No. 5, Part 2, p. 876–877.

Csonka, Laszlo N., Physiological and Genetic Responses of Bacterial to Osmotic Stress, *Microbiological Reviews*, 1989, vol. 53, No. 1, p. 121–147.

Brayton, P.R., Enumeration of *Vibrio cholerae* 01 in Bangladesh Waters by Fluorescent–Antibody Direct Viable Count, *Applied and Environmental Microbiology*, 1987, vol. 53, No. 12, p. 2862–2865.

Burke, Victor, et al., Dormancy in Bacteria, *J. Infect. Dis.*, 1925, vol. 35, p. 555–560.

\* cited by examiner

*Primary Examiner*—David M. Naff
*Assistant Examiner*—Deborah K. Ware
(74) *Attorney, Agent, or Firm*—McKee, Voorhees & Sease, P.L.C.

(57) ABSTRACT

A method for arousing dormant bacteria. The method comprises inducing diffusion of intracellular solutes from dormant bacteria and then allowing an adjustment period for a length of time sufficient to initiate arousal. The decrease in intracellular osmolality or pH can be induced by methods such as extraction, dilution, or dialysis. The method has been standardized using Dulbecco's phosphate buffered saline as the solution. The aroused bacteria can then be selected or recovered by growing them on media for a period of time. If the adjustment period is prolonged, many bacteria can become hypermutative.

3 Claims, No Drawings

METHODS FOR AROUSING DORMANT BACTERIA

FIELD OF THE INVENTION

This invention relates to methods and compositions for arousing dormant bacteria. More particularly, this invention relates to methods and compositions for arousing dormant bacteria for the purpose of detecting their presence, evaluating their threat to health, and, if warranted, killing them. Even more particularly, the invention relates to arousing dormant bacteria by altering their internal osmolality and/or pH and allowing adjustment time for the arousal mechanism to be initiated.

BACKGROUND OF THE INVENTION

Dormant populations of bacteria are formed during the normal growth cycles of non-spore forming genera. Dormant bacteria were first described in 1925 as cells formed during the stationary phase of normal microbial growth (Burke, Sprague & Barnes, *J. Inf. Dis.*, 36:555–560 (1925)). By definition, they do not grow on nutrient-rich media selected for their proliferation and classification. Since growth on selected media defines viability, confusion and disbelief continue to surround the existence of dormant bacteria. The phrase "viable but not culturable" (VBNC) is frequently used as a descriptor.

Dormancy is different from sporulation. Late in the stationary phase vegetative cells of the genera Bacillus and Clostridium form spores, dense particles resistant to adverse conditions. For example, Clostridial spores can withstand 100° C. for more than one hour, therefore, saturated steam at 121° C. for 15 minutes is required to kill them. Germination of these spores is induced by heating neutral suspensions of these cells at 65° C. for 20 minutes. If L-alanine, L-tyrosine, or adenosine is added to the buffer, 100% of the spores will germinate.

Dormant bacteria are believed to form in response to environmental stressors that are not part of their normal growth cycle. Dormant bacteria form during the normal growth cycle for both harmless and pathogenic isolates of Gram-positive and Gram-negative bacteria Thus these non-detectable dormant bacteria have the potential to be widespread threats to human health. Their presence is suspicioned in recurring illness in patients and endemics. The spread of cholera has been in part attributed to dormant forms of *V cholera* in potable water. Brayton, P. R., et al. (1987) *Appl. Envir. Micro.* 53:2862. The outbreak of Legionella infections in Philadelphia in 1976 is believed to have resulted from the arousal of dormant *L. pneumophila* residing in a hotel's air conditioning system. Steinert, M., et al. (1997) *Appl. Envir. Micro.* 63:2047. Endogenous dormant *M. tuberculosis* are thought to be responsible for recurrent tuberculosis. Hu, Y. M., et al. (1998) *FEMS Micro LETT* 158:139. Dormant *Shigella dysenteriae* produce diarrhea when orally administered to humans. Rahman, I., et al. (1994) *Apl. Envir. Micro.* 60:3573. Quiescent bacteria may be aroused during in vitro fertilization and embryo transfer. Peters, A. J., et al. *Ob & Gyn* 81:876 (1993).

Quiescent bacteria may be aroused during in vitro fertilization and embryo transfer. Peters, A. J., et al. *Ob & Gyn* 81:876 (1993).

Methods to "resuscitate" dormant bacteria have been identified for several genera or species, namely *V. cholera, V. vulnificus, M. luteus, L. pneumophila, M. tuberculosis*, and *Nitrosomonas*. Dormancy was induced by placing small amounts of vegetative cells into life-threatening conditions, such as nutrient or oxygen deprivation or low temperature environments for long periods, e.g. 125 days. Cells were resuscitated by restoring normal or rich conditions or by passing dormant bacteria through their parasitic or animal hosts. U.S. Pat. No. 5,314,542 discloses packaging bacteria from the genus *Nitrosomonas* in such a way as to induce dormancy, then reactivating these bacteria by increasing the concentration of their key nitrogen nutrient, ammonia, to 200 ppm and holding for 72 hours. To date, no one general method can be applied broadly to multiple species of bacteria.

For the foregoing reasons, a need exists for a generally-adaptable method to arouse dormant bacteria.

SUMMARY OF THE INVENTION

An object of this invention is to provide a method for arousing dormant bacteria.

Another object of this invention is to provide a method for recovering aroused, previously dormant bacteria from a culture for purposes such as classification, killing, or prevention of proliferation.

These and other objects, features, and advantages will become apparent after review of the following description and claims of the invention which follow.

This invention comprises a method for arousing dormant (non-spore forming) bacteria. The purposes of arousal include, for example, classification, killing, or prevention of proliferation in susceptible hosts.

Dormant bacteria are formed during the stationary phase of a normal growth cycle of both Gram-positive and Gram-negative species, both pathogenic and harmless species, and both feral and lab isolates. After proliferation, nonspore-forming bacteria may enter into a state of dormancy, and neither grow on media nor die in unfavorable environments. Although metabolically active, dormant bacteria are tolerant to antibiotics, chemicals, and other toxicants. Arousal can be induced by decreasing the internal osmolality, and thereby, the internal water activity of the cell ($a_w$), or by neutralizing the internal pH.

The changes in osmolality or pH required for arousal are initiated by forcing the cell to diffuse its solutes or hydrogen ions into the media environment in a prescribed series of exposures to osmolal downshift gradients and providing for periods of adjustment. In other words, the internal osmolality of the dormant bacterial cell is decreased, and the cell is allowed to adjust to these changes gradually. During the adjustment period, the cell prepares to initiate replication. If the adjustment period is extended beyond that required for the initiation of growth, the cell can become hypermutative, as demonstrated by an ability to tolerate lethal doses of antibiotics without having been primed by exposures to less than lethal levels.

Different species require different adjustment periods and different rates of diffusion of internal solutes to maximize arousal. In addition, although just neutralizing the internal pH can be sufficient to induce arousal, an adjustment period of 10 days or more may be necessary to induce growth even in cultures that are easily aroused. When rates of diffusion and periods of adjustment are optimally controlled, the maximum number of dormant cells are aroused in the shortest amount of time. Too sudden diffusion from a gradient of too great an intensity will not induce arousal. On the other hand, if diffusion is too slow, arousal requires long periods of adjustment before arousal occurs.

The extent of downshift gradients and the length of the adjustment period required to arouse the maximum number of dormant cells in the shortest time is species dependent. Some, like *L. monocytogenes* is readily aroused, and others, like *L. plantarum* require extensive treatment before arousing. However, the present invention teaches a general method that arouses easily-arousable bacteria and provides guidance for arousing more difficult ones.

Definitions

"Dormant" bacteria as used herein includes (a) bacterial cells that are "viable but not culturable" or "quiescent" or "nascent" which are (b) metabolically active, but (c) do not propagate in broths or on agar media formulated for their growth and identification.

"Arousing" as used herein includes causing dormant cells to propagate in broths or an agar media developed for their growth and identification.

The "vegetative" form of dormant bacteria, as used herein, is that form of the dormant cells which grows on appropriate media.

"Hypermutative" dormant cells are those that during arousal phase develop the ability to proliferate in the presence of lethal levels of an antibiotic to which they were not previously exposed.

DETAILED DESCRIPTION OF THE PREFERRED EMBODIMENT

Non-spore forming bacteria form dormant cells during the stationary phase of a normal growth cycle. Like spores, dormant cells proliferate in response to a specific physical change in their environment. Whereas heat provokes the biological change in spores that results in their germination, gradients of osmotic downshifts trigger the transformation of dormant cells to their vegetative forms and, if prolonged, to their hypermutative forms.

During the stationary phase, the cell accumulates small molecules, acids and other solutes, thereby increasing its osmotic pressure, lowering its water activity ($a_w$) and, thus, halting cell division yet continuing some metabolic functions. The population of dormant cells in a duplex culture-a culture containing both living forms-can be as high as $10^7$ colony-forming units (CFUs) per mL. In an older, "nonculturable" culture, dormant cells were found to average about $10^5$ CFUs per mL. Arousal occurs when the high $a_w$ of the cell returns.

Subjecting bacteria or specimens to environments of osmolality of less than that of the cell followed by adjustment periods will arouse dormant bacteria. Such osmotic gradients can be accomplished any number of ways. Three preferred methods are 1. sequential diffusion (series of extractions),
2. progressive diffusion (sequential dilution), and
3. continuous diffusion (dialysis).

Although various buffers of osmolality less than that internal to the cell can be used, including media or those containing nutrients, the method has been standardized with phosphate buffered saline (Dulbecco's PBS, pH 7.3, 0.8% NaCl)—a solution well known in microbiology.

This method was developed by first killing vegetative cells, inducing dormancy by extending the normal growth cycle of representative bacterial species, and then arousing feral and lab isolates of *L. monocytogenes, L. caseii, L. plantarum, P. aeruginosa*, and *E. coli*. By optimizing the parameters of downshift gradients of osmolality and the adjustment periods required for arousal, the general method developed can be adapted by one skilled in the art to assay any specimens taken from animals or terrestrial environments.

The arousal phase requires three periods: a downshift period, during which the internal osmolality is reduced at neutral pH, an adjustment period in which the cell prepares to initiate cell division, and a grow-out period on appropriate agar. The downshift gradients can be applied in a number of different ways depending on the skill of the operator and the convenience and availability of equipment. Some examples include:

1. a series of extractions over 20 minute time periods.
2. a series of sequential dilutions at increasing ratios from 1:5 to 1:1000.
3. dialysis against 250 volumes of buffer.

By applying these methods to test bacteria, the dormant forms are present in non-viable cultures at levels from $10^3$ to $10^7$ CFUs per mL. Viable cultures in their stationary phase can contain as many as $10^7$ dormant cells, 0.1–10% of the viable population. Non-viable cultures may contain $10^5$ dormant cells.

The preferred embodiment for progressive diffusion (dilution) is the 1:5 dilution, adaptive rest, 1:25 dilution, and 1:125 dilution. Four volumes of PBS, pH 7.3 are added to one volume of liquid specimen and allowed to adapt for a period of 24 hours at 37° C. before being diluted twice again at 1:5. The 1:125 dilution is streaked on appropriate media to demonstrate viability and on agar plus antibiotic to demonstrate hypermutativeness.

The preferred method for sequential diffusion (extraction) is a series of 20 minute periods. The liquid specimen is microfuged. The pellet is suspended in PBS and allowed to diffuse for 20 minutes at 37° C. before again microfuging and resuspending in fresh PBS. This is repeated up to 6 times and the suspension streaked on appropriate media with and without antibiotics.

The preferred method for continuous diffusion is as follows. For simple dialysis, the liquid specimen is placed in a washed dialysis bag with cutoff of 6–8 kDa and dialyzed against 250 volumes of PBS at 37° C. with stirring for 40 minutes. The retentate is removed and allowed to adapt overnight before diluting 1:5 twice with PBS and streaking on appropriate agar. For centrifugal dialyis, the liquid suspension is centrifuged in a Centriplus® 10 tube (Millipore, Inc., Bedford, Mass.) at 3000 xg at room temperature for 30 minutes. The diffusate is removed and replaced with an equal volume of PBS added to the retentate and the centrifugation is repeated. The centrifugation and replacement of the diffusate is repeated Aroused dormant cells become hypermutative if held for prolonged periods in the adjustment period during or after the downshift period. They can become tolerant to antibiotics and low-nutrient environments. Viable cells are not harmed by these forced diffusions, in fact, vegetative cells so treated can also become hypermutative.

In a mixture of vegetative and dormant cells, one can determine the levels and classification of dormant cells by first subjecting the mixture to killing conditions (e.g., heating at 100° C.) and then arousing the dormant cells by following the above procedures of downshift gradients, adjustment, and grow-out periods.

After proliferation, non-spore forming bacteria can enter into a state of dormancy in which they are metabolically active but do not grow on appropriate media nor die when subjected to environments which kill their vegetative forms. A fundamental method to arouse dormant bacteria is useful for detection and classification and killing, if appropriate. On the other hand, useful food cultures can be kept "alive" by avoiding conditions that arouse their dormancy.

Reduction of cells' water activity ($a_w$) and adjustment of the internal pH induces arousal. This is accomplished by 1. extracting solutes and $H^+$ ions from the cell
2. allowing time to initiate the growth processes and the induction of mutativeness, and
3. providing time for their grow-out.

Arousal follows the suspension of dormant cells in an environment which induces the desorption of molecules from the cell. However, the rate of diffusion must be within a species-defined range, neither too severe or too gradual. For example, dormant cells of *L. monocytogenes*, a foodborne pathogen, are easily aroused by extracting the dormant cells in buffer for 20 minutes and growing them out overnight. They become hypermutative if extracted 3 times and allowed to adjust for 72 hours. Dormant cells of *L. caseii*, a dairy food culture, are aroused only if extracted 3 times, and do not become hypermutative. Dormant cells of *L. plantarum*, a harmless fresh vegetable organism, requires 7 extractions and an adjustment period of 144 hours to become aroused. Like *L. caseii* it appears not to possess the ability to become hypermutative.

Furthermore, dormant *L. caseii* is aroused if extracted with either 1× or 4× Dulbecco's PBS, but not in water. The arousal mechanism is triggered by a lowering of the cell's osmolality, but the optimum gradient is species-dependent.

In addition, dilutions of 1:5 may arouse more cells of a species than dilutions of 1:2 or 1:100 over the same time period. Some cells will be aroused after one dilution of 1:5 followed by an adjustment period of 24 hours. Other species may require additional dilutions, while still others require long adjustment periods, e.g., 72 hours.

Four subsequent dialyses against 250 volumes of buffer will arouse *L. plantarum*, but one dialysis against 1000 volumes will not.

Initiating hypermutativeness in all tested cells required adjustment periods longer than those required for arousal.

The length of time that a culture had been dormant did not appear to influence its conditions for arousal, nor did the temperature under which it became dormant, e.g., 4° C., 25° C., or 37° C.

It is useful to employ the General Method in the first attempt to determine the presence of dormant bacteria. With results, refinements can be made as taught herein and claimed.

Arousal in the general method has three sequential periods:

1. a Downshift Period, in which the bacteria are placed in an environment that induces a gradual decrease in the cell's internal osmolality at a constant rate. This is done by exposing the cells to solutions of lower osmolalities for specific periods of time by extraction, dilution, dialysis, or similar methods which expose the cells to the solution. Molecules diffusing out of the cell release the constraints on the arousal mechanism. Buffers of neutral pH are more effective than acidic ones.

2. an Adjustment Period, in which biological reactions are induced in the cell after reduced osmolality. Adjustment begins during the downshift period and continues through the subsequent grow-out period. Bacterial cells, both dormant and vegetative become hypermutative during an adjustment period of 72–140 hours.

3. the Grow-out Period is the elapsed time between plating and the appearance of colonies. Vegetative colonies can appear overnight; mutants require up to 160 hours at 37° C. Gram-positive viable cells are not killed nor proliferate by being subjected to downshift gradients for periods of days. Like aroused cells, they become hypermutative during an extended adjustment period. However, Gram-negative cells appear to be sensitive to downshifting. Unless transferred to media within 36 hours after being extracted 7 times with PBS, viable cells of *P. aeruginosa* and *E. coli* die. However, dormant cells of these species are aroused after 7 extractions and an adjustment period of 72 hours. But now, being in the vegetative state, their survival time is also limited to 36 hours. One needs to, therefore, be mindful of these differences and how the general methods can optimize arousals on a species-specific basis. This differential can be used to determine the existence of dormant forms in the presence of vegetative forms of Gram-negative genera.

Since the arousal of dormant bacteria is species-specific and specimens of interest may contain unknown species and mixtures of dormant species, the general method should be used for initial analysis. Subjecting dormant cultures to sequential extractions has been selected as an efficient and effective arousal method for general use. The parameters chosen are those which were found to arouse all the test bacteria and provoke hypermutativeness in capable isolates. Subsequent analyses can then be performed by any of the examples or combinations of affecting downshift osmolar gradients.

1. centrifuge the bacterial pellet and resuspend in an equal volume of Dulbecco's PBS, pH 7.3 for 20 minutes at 37° C. Repeat for a total of 7 extractions. Hold aliquots of the $3^{rd}$, $6^{th}$, and $7^{th}$ extractions at 37° C. for adjustment.

2. after an adjustment period of 3 days and 6 days, streak the 3 extractions on appropriate agar media and incubate at 37° C. Observe growth of aroused and hypermutative cells for 5 days.

The following examples are offered to illustrate, but not limit the invention.

EXAMPLE 1

Induction of Dormancy

Pure and mixed cultures of *L. monocytogenes*, *L. caseii*, *L. plantarum*, *E. coli*, *P. aeruginosa* were rendered partially or totally dormant by growing through stationary phase in appropriate media:

TABLE 1

| Culture | Media |
| --- | --- |
| Listeria sp. | Brain-heart-infusion (BHI) |
| Lactic acid bacteria | Mann-Rogosa-Sharp (MRS) |
| Gram-negative bacteria | Tryptic soy broth (TSB) | at 37° C. The number of viable colonies fell to less than detectable, i.e., <100 CFUs per mL. The time to form a monoculture of dormant cells was species-dependent, but was usually between 90 and 500 days at 37° C.

TABLE 2

| Species | Days for Dormancy |
| --- | --- |
| L. monocytogenes | 400–500 |
| L. caseii | 100–200 |
| L. plantarum | 100–150 |
| E. coli | 150–200 |
| P. aeruginosa | 150–200 |

The population of dormant forms in these cultures is shown in TABLE 3.

TABLE 3

| Species | Population |
| --- | --- |
| L. monocytogenes | $10^4$–$10^5$ |
| L. caseii | $10^4$–$10^5$ |
| L. plantarum | $10^4$–$10^5$ |
| E. coli | $10^3$–$10^4$ |
| P. aeruginosa | $10^2$–$10^3$ |

EXAMPLE 2

Effect of Phosphate-Buffered Saline (PBS) on the Viability of Vegetative Cells Seventy-five percent of the populations of gram-positive, broth-grown vegetative cells remain viable after 3 sequential two-hour extractions in Dulbecco's at pH 7.3.

TABLE 4

L. monocytogenes transferred from Broth in Stationary Phase

| Population Before Extraction | Population after Time in Dulbecco's (CFUs/mL) | | |
|---|---|---|---|
| (CFU/mL) | 2 hrs. | 4 hrs. | 6 hrs. |
| $1.15 \times 10^8$ | $1.0 \times 10^8$ | $9 \times 10^7$ | $7 \times 10^7$ |
| $5.2 \times 10^7$ | $4.0 \times 10^7$ | $3.2 \times 10^7$ | $2.4 \times 10^7$ |

(n = 35, range −90% to +40%)

Ninety-five percent of the population of gram-positive, agar-grown vegetative cells remain viable after 3 sequential two-hour extractions in Dulbecco's at pH 7.3.

TABLE 5

L. monocytogenes transferred from Agar in Stationary Phase

| Population before extraction | Population after time in Dulbecco's (CFUs/mL) | | |
|---|---|---|---|
| (CFU/mL) | 2 hrs. | 4 hrs. | 6 hrs. |
| $4.1 \times 10^8$ | $4.1 \times 10^8$ | $3.85 \times 10^8$ | — |
| $3.3 \times 10^8$ | $3.3 \times 10^8$ | $3.25 \times 10^8$ | $3.3 \times 10^8$ |
| $2.9 \times 10^8$ | $2.9 \times 10^8$ | $3.3 \times 10^8$ | $3.0 \times 10^8$ |

(n = 10, range, −25 to +5%)

Gram-negative vegetative cells are sensitive to downshifting. Unless transferred to media within 48 hrs. after repeated exposure to PBS, both *P. aeruginosa* and *E. coli* lost viability.

TABLE 6

*P. aeruginosa*, $10^5$ CFUs/mL transferred from Broth in Stationary Phase

| Osmolal Gradients | Adjustment Time (hrs.) | Population (CFUs/mL) |
|---|---|---|
| None | 0 | $10^5$ |
| 3 × 20 min. | 0 | $10^5$ |
| 3 × 20 | 24 | $10^3$ |
| 3 × 20 | 48 | ND |
| 7 × 20 | 0 | $10^5$ |
| 7 × 20 | 48 | ND |

ND = none detected

TABLE 7

*E. coli*, $10^5$ CFUs/mL Transferred from Broth in Stationary Phase

| Osmolal Gradients | Adjustment Time (hrs.) | Population (CFUs/mL) |
|---|---|---|
| None | 0 | $10^5$ |
| 3 × 20 min. | 0 | $10^5$ |
| 3 × 20 | 24 | $10^4$ |

TABLE 7-continued

*E. coli*, $10^5$ CFUs/mL Transferred from Broth in Stationary Phase

| Osmolal Gradients | Adjustment Time (hrs.) | Population (CFUs/mL) |
|---|---|---|
| 3 × 20 | 48 | ND |
| 7 × 20 | 0 | $10^5$ |
| 7 × 20 | 48 | ND |

Both native vegetative and aroused dormant cells of *L. monocytogenes* were tolerant to 60 IU of ampicillin per mL (amp/mL). However, tolerance to 30 μg of tetracycline per mL (TC/mL) occurred only in those vegetative or aroused dormant cells after adjustment times of 72 to 96 hrs. in PBS, as shown in Example 4, TABLE 14.

EXAMPLE 3

Dormant Bacteria Under Heat-killing Conditions

Dormant cells of *L. monocytogenes* survived and were not aroused by pasteurization, 63° C. for 30 min. However, dormant forms were affected by heat, requiring fewer extractions and longer adjustment times and grow-out periods to establish visible colonies on agar. In addition, heat-treated aroused dormant cells did not become tolerant to tetracycline.

TABLE 8

Survival of 3 Week Old Broth Culture of *L. monocytogenes* at 63° C.

| | Vegetative cells | | Dormant Cells | |
|---|---|---|---|---|
| Time (min.) | Population (CFUs/mL) | Osmolal Gradient | Adjustment Time (hrs.) | Population (CFUs/mL) |
| 0 | $7 \times 10^8$ | — | — | — |
| 10 | $8 \times 10^7$ | — | — | — |
| 15 | $8 \times 10^4$ | — | — | — |
| 25 | $2 \times 10^3$ | 2 × 20 min. | 24 | $10^5$ |
| 45 | $1 \times 10^3$ | 1 × 20 | 72 | $10^5$ |
| 45 | $1 \times 10^3$ | 2 × 20 | 72 | $2 \times 10^3$ |

The differential in heat-tolerance observed between dormant and vegetative cells can be used to determine the presence of dormant cells in a culture containing vegetative cells.

The culture is subjected to the pasteurization temperature of 63° C., until the population of vegetative cells falls to fewer than 1000 CFUs/mL or less than the level of dormant cells. The pellet is recovered by centrifugation and extracted with PBS for 20 min. at 37° C., before centrifuging again and adding fresh PBS to the pellet and allowing to stand for 72 hrs. at 37° C. Aliquots are taken at 24, 48 and 72 hrs. for pour-plating in appropriate agar media. Surface colonies of aroused dormant cells appear within 7 days at 37° C., which then can be classified.

Heat-treated aroused cells may have a biochemistry profile different from non-heat-treated aroused cells or their vegetative forms, e.g., a coagulase-positive *S. aureus* became coagulase negative; a *L. innocua* may type out on API as an abnormal Listeria, code 7000.

Aroused *L. monocytogenes* have characteristics different from their vegetative cells. These differences can be used to identify aroused dormant cells in the presence of their vegetative populations. For example, the aroused forms were unable to lyse red blood cells, but readily became tolerant to lethal doses of tetracycline.

TABLE 9

Classification of Vegetative and Aroused *L. monocytogenes*

| Characteristic | Vegetative | Aroused Dormant |
|---|---|---|
| Morphology | Small, translucent | Large, opaque |
| Gram stain | Positive | Can be decolorized |
| Mobility | Tumbling at RT | Tumbling at RT |
| Oxidase | Negative | Negative |
| Catalase | Positive | Positive |
| Hemolysis | Positive | Negative |
| API | 6510 | Not 6510 |
| TC 30 µg/mL | Susceptible | Tolerant |

RT = room temperature

API is a test kit sold by bioMérieux, Inc. (St. Louis, Mo.) for identifying bacteria. A numeric result of 6510 indicates that the strain is a classic *L. monocytogenes*; other numbers indicate species of Listeria other than *monocytogenes*.

Dormant cells of *S. aureus* could be enumerated and classified in the presence of their vegetative forms by heat-killing the sensitive vegetative forms while preserving the more resistant dormant forms. In addition, the aroused dormant forms showed tolerance to 30 µg vancomycin/mL, as did the untreated vegetative form. Before heating, $4 \times 10^7$ CFUs/mL were viable, after heating, no viable cells were detected until the dormant cells were aroused by osmolal downshift gradients.

TABLE 10

Survival of Dormant *S. aureus* after 1 min. at 100° C.

| Osmolal Gradients | Adjustment Time (hrs.) | Population (CFU/mL) |
|---|---|---|
| 1 × 20 min. | 24 | 6 |
| 1 × 20 | 48 | $1.3 \times 10^4$ |

EXAMPLE 4

Arousing Dormant Bacteria by Sequential Extractions to Effect a Downshift Gradient The arousal phase has 3 periods: downshifting of osmolality, adjustment, and grow-out. Optimum conditions are species-specific.

A culture containing 100% dormant bacteria was microfuged and the supernatant replaced with an equal volume of PBS, pH 7.3 and incubated at 37° C. After 20 minutes, the pellet was again recovered by centrifugation and resuspended in fresh PBS.

TABLE 11

Dormant *L. monocytogenes* sequential extraction.

| Extraction | Growth (CFUs/mL) | Growth in presence of ampicillin (CFUs/mL) |
|---|---|---|
| Control | 0 | 0 |
| 1st 20 min. | $10^4$ | $10^4$ |
| 2nd 20 min. | $10^5$ | $10^4$ |
| 3rd 20 min. | $10^5$ | $10^4$ |
| 4th 20 min. | $10^5$ | $10^5$ |

TABLE 11-continued

Dormant *L. monocytogenes* sequential extraction.

| Extraction | Growth (CFUs/mL) | Growth in presence of ampicillin (CFUs/mL) |
|---|---|---|
| 5th 20 min. | $10^5$ | $10^5$ |
| 6th 20 min. | $10^6$ | $10^5$ |

TABLE 12

Dormant *L. caseii* sequential extraction.

| Extraction | Growth (CFUs/mL) | Growth in presence of 60 IU/mL ampicillin (CFUs/mL) |
|---|---|---|
| Control | 0 | 0 |
| 1st–5th 20 min. | 0 | 0 |
| 6th 20 min. + 72 hrs. @ 37° C. | $10^3$ | 0 |
| 6th 20 min. + 96 hrs. @ 37° C. | $10^4$ | 0 |

Extracting with PBS, pH 6.1 aroused fewer than 10% of the cells, compared to those aroused with pH 7.3. Extracting with PBS, pH 8.0 aroused nearly as many dormant cells as did extraction with pH 7.3.

TABLE 13

Dormant *L. monocytogenes* sequential extraction.

| pH | Extraction | Growth (CFUs/mL) |
|---|---|---|
| 6.1 | 3rd 20 min | $6 \times 10^3$ |
| 7.3 | 3rd 20 min | $1 \times 10^5$ |
| 8.0 | 3rd 20 min | $5 \times 10^4$ |

A 4 year old dormant broth culture of *L. monocytogenes* was centrifuged and the supernatant replaced with an equal volume of Dulbecco's PBS, 1×, 4×, or 10×, pH 7.3 or 6.1 for 10, 20, or 40 min. extraction periods, followed by different periods of adjustment at 37° C. This was repeated and the pellets held for various times in buffer (adjustment period) before plating on agar. Inoculated agars were held at 37° C. for various lengths of time (grow-out period).

TABLE 14

Growth of *L. monocytogenes* after downshifts with Dulbecco's PBS at pH 7.3.

| Osmolar gradients | Adjustment Time (hrs.) | Growth on BHI (hrs.) | Growth in presence of 60 IU amp/mL (hrs.) | Growth in presence of 30 µg TC/mL (hrs.) |
|---|---|---|---|---|
| 5 × 10 min. | 0 | ND | ND | ND |
| 5 × 10 min. | 48 | ND | ND | ND |
| 5 × 10 min. | 96 | 24 | 24 | 72 |
| 6 × 10 min. | 0 | 48 | 48 | ND |
| 1 × 20 min. | 0 | 48 | 48 | ND |
| 3 × 20 min. | 0 | 48 | 48 | ND |
| 6 × 20 min. | 0 | 48 | 48 | ND |
| 9 × 20 min. | 0 | 48 | 48 | ND |
| 3 × 20 min. | 48 | 24 | 48 | ND |
| 6 × 20 min. | 48 | 24 | 48 | ND |
| 9 × 20 min. | 48 | 24 | 48 | ND |
| 3 × 20 min. | 72 | 24 | 48 | 96 |
| 6 × 20 min. | 72 | 24 | 48 | 96 |

TABLE 14-continued

Growth of *L. monocytogenes* after downshifts with Dulbecco's PBS at pH 7.3.

| Osmolar gradients | Adjustment Time (hrs.) | Growth on BHI (hrs.) | Growth in presence of 60 IU amp/mL (hrs.) | Growth in presence of 30 μg TC/mL (hrs.) |
|---|---|---|---|---|
| 9 × 20 min. | 72 | 24 | 48 | 96 |
| 3 × 40 min. | 0 | ND | ND | ND |
| 3 × 40 min. | 96 | 24 | 24 | 24 |
| 7 × 40 min. | 0 | ND | ND | ND |
| 7 × 40 min. | 96 | 24 | 48 | 48 |

ND = growth not detected

TABLE 15

Growth of *L. monocytogenes* after downshifts with Dulbecco's 4X PBS at pH 7.3.

| Osmolal gradients | Adjustment Time (hrs.) | Growth on BHI (hrs.) | Growth in presence of 60 IU amp/mL (hrs.) | Growth in presence of 30 μg TC/mL (hrs.) |
|---|---|---|---|---|
| 3 × 20 min. | 0 | ND | ND | ND |
| 3 × 20 min. | 48 | 24 | 24 | ND |
| 3 × 20 min. | 72 | 24 | 24 | 72 |

TABLE 16

Growth of *L. monocytogenes* after downshifts with Dulbecco's 10X PBS at pH 7.3.

| Osmolal gradients | Adjustment Time (hrs.) | Growth on BHI (hrs.) | Growth in presence of 60 IU amp/mL (hrs.) | Growth in presence of 30 μg TC/mL (hrs.) |
|---|---|---|---|---|
| 3 × 20 min. | 0 | ND | ND | ND |
| 3 × 20 min. | 48 | 24 | 24 | ND |
| 3 × 20 min. | 72 | 24 | 24 | 72 |

TABLE 17

Growth of *L. monocytogenes* after downshifts with Dulbecco's PBS at pH 6.1.

| Osmolal gradients | Adjustment Time (hrs.) | Growth on BHI (hrs.) | Growth in presence of 60 IU amp/mL (hrs.) | Growth in presence of 30 μg TC/mL (hrs.) |
|---|---|---|---|---|
| 1 × 20 min. | 0 | ND | ND | ND |
| 2 × 20 min. | 0 | 48 | ND | ND |
| 7 × 20 min. | 96 | 24 | 24 | ND |
| 5 × 20 min. | 120 | 24 | 24 | 96 |

A 2 year old dormant broth culture of *L. caseii* was centrifuged and the supernatant replaced with an equal volume of Dulbeccos' PBS, 1× or 4× at pH 7.3, or water for 20 min. followed by different periods of adjustment at 37° C.

TABLE 18

Growth of *L. caseii* ATCC 393 after downshifts with Dulbecco's PBS at pH 7.3.

| Osmolal gradients | Adjustment Time (hrs.) | Growth on MRS (hrs.) | Growth in presence of 60 IU amp/mL (hrs.) | Growth in presence of 30 μg TC/mL (hrs.) |
|---|---|---|---|---|
| 7 × 20 min. | 0 | ND | ND | ND |
| 7 × 20 min. | 96 | 24 | ND | ND |
| 7 × 20 min. | 144 | 24 | 48 | ND |

TABLE 19

Growth of *L. caseii* ATCC 393 after downshifts with Dulbecco's 4X PBS at pH 7.3.

| Osmolal gradients | Adjustment Time (hrs.) | Growth on MRS (hrs.) | Growth in presence of 60 IU amp/mL (hrs.) | Growth in presence of 30 μg TC/mL (hrs.) |
|---|---|---|---|---|
| 3 × 20 min. | 0 | ND | ND | ND |
| 3 × 20 min. | 72 | 24 | ND | ND |
| 3 × 20 min. | 96 | 24 | ND | ND |
| 3 × 20 min. | 140 | 24 | ND | ND |

TABLE 20

Growth of *L. caseii* ATCC 393 after downshifts with water.

| Osmolal gradients | Adjustment Time (hrs.) | Growth on MRS (hrs.) | Growth in presence of 60 IU amp/mL (hrs.) | Growth in presence of 30 μg TC/mL (hrs.) |
|---|---|---|---|---|
| 7 × 20 min. | 0 | ND | ND | ND |
| 7 × 20 min. | 72 | ND | ND | ND |
| 7 × 20 min. | 96 | ND | ND | ND |
| 7 × 20 min. | 144 | ND | ND | ND |

Dormant cultures of feral- and ATCC-sourced *L. plantarum* were centrifuged and the supernatants replaced with equal volumes of Dulbecco's PBS, at pH 7.3, for 20 min. followed by different periods of adjustment at 37° C.

TABLE 21

Growth of *L. plantarum* ATCC 14917 after downshifts with Dulbecco's PBS at pH 7.3.

| Osmolal gradients | Adjustment Time (hrs.) | Growth on MRS (hrs.) | Growth in presence of 60 IU amp/mL (hrs.) | Growth in presence of 30 μg TC/mL (hrs.) |
|---|---|---|---|---|
| 7 × 20 min. | 0 | ND | ND | ND |
| 3 × 20 min. | 96 | ND | ND | ND |
| 7 × 20 min. | 72 | ND | ND | ND |
| 7 × 20 min. | 144 | 96 | ND | ND |

TABLE 22

Growth of *L. plantarum* feral isolate after downshifts with Dulbecco's PBS at pH 7.3.

| Osmolal gradients | Adjustment Time (hrs.) | Growth on MRS (hrs.) | Growth in presence of 60 IU amp/mL (hrs.) | Growth in presence of 30 μg TC/mL (hrs.) |
|---|---|---|---|---|
| 7 × 20 min. | 0 | ND | ND | ND |
| 3 × 20 min. | 96 | ND | ND | ND |
| 7 × 20 min. | 72 | ND | ND | ND |
| 7 × 20 min. | 144 | 96 | ND | ND |

Separate cultures containing both dormant and vegetative cells of *P. aeruginosa* or *E. coli* were centrifuged and the pellets resuspended in an equal amount of Dulbecco's PBS pH 7.3 for serial extractions of 20 min. followed by different periods of adjustment at 37° C.

TABLE 23

Growth of duplex culture of *P. aeruginosa* after downshifts with Dulbecco's PBS at pH 7.3.

| Osmolal gradients | Adjustment Time (hrs.) | Growth on MRS (hrs.) | Growth in presence of 60 IU amp/mL (hrs.) | Growth in presence of 30 μg TC/mL (hrs.) |
|---|---|---|---|---|
| 3 × 20 min. | 0 | 48 | ND | ND |
| 3 × 20 min. | 24 | 72 | 72 | ND |
| 3 × 20 min. | 48 | ND | ND | ND |
| 3 × 20 min. | 72 | ND | ND | ND |
| 6 × 20 min. | 0 | 48 | 48 | ND |
| 6 × 20 min. | 24 | 48 | ND | ND |
| 6 × 20 min. | 48 | ND | ND | ND |
| 6 × 20 min. | 72 | 72 | ND | ND |
| 6 × 20 min. | 96 | ND | ND | ND |

TABLE 24

Growth of duplex culture of *E. coli* ATCC 11775 after downshifts with Dulbecco's PBS at pH 7.3.

| Osmolal gradients | Adjustment Time (hrs.) | Growth on MRS (hrs.) | Growth in presence of 60 IU amp/mL (hrs.) | Growth in presence of 30 μg TC/mL (hrs.) |
|---|---|---|---|---|
| 3 × 20 min. | 0 | 48 | ND | ND |
| 3 × 20 min. | 24 | 24 | ND | ND |
| 3 × 20 min. | 48 | ND | ND | ND |
| 3 × 20 min. | 72 | ND | ND | ND |
| 6 × 20 min. | 0 | 48 | ND | ND |
| 6 × 20 min. | 24 | 48 | ND | ND |
| 6 × 20 min. | 48 | ND | ND | ND |
| 6 × 20 min. | 72 | 72 | ND | ND |
| 6 × 20 min. | 96 | ND | ND | ND |

A culture containing both dormant *L. caseii* and dormant *E. coli* was centrifuged and the pellet resuspended in Dulbecco's PBS, pH 7.3, for serial extractions of 20 min. followed by different periods of adjustment at 37° C.

TABLE 25

Growth of mixed culture of dormant *L. caseii* and *E. coli* after downshifts with Dulbecco's PBS at pH 7.3.

| Osmolar gradients | Adjustment Time (hrs.) | Growth on MRS (hrs.) | Growth in presence of 60 IU amp/mL (hrs.) | Growth in presence of 30 μg TC/mL (hrs.) |
|---|---|---|---|---|
| 3 × 20 min. | 0 | ND | ND | ND |
| 3 × 20 min. | 24 | ND | ND | ND |
| 3 × 20 min. | 48 | ND | ND | ND |
| 3 × 20 min. | 72 | ND | ND | ND |
| 6 × 20 min. | 0 | ND | ND | ND |
| 6 × 20 min. | 24 | ND | ND | ND |
| 6 × 20 min. | 48 | ND | ND | ND |
| 6 × 20 min. | 72 | 48 | ND | ND |
| 6 × 20 min. | 144 | 48 | ND | ND |

It was concluded that dormant populations of different genera require different conditions of osmolal downshifting and adjustment times to fully arouse the maximum numbers of dormant forms and to render them hypermutative. The viability of aroused dormant gram-negative cells appears to be more sensitive to long adjustment periods than gram-positive cells.

In summary the preferred embodiments are as follows:

TABLE 26

| Culture | Extractions | Adjustment Period (hrs.) For arousal | For hypermutation |
|---|---|---|---|
| *L. monocytogenes* | 1 × 20 | 0 | None |
|  | 3 × 20 | 72 | 96 |
|  | 3 × 40 | 96 | 24 |
| *L. caseii* 4X PBS | 3 × 20 | 72 | None |
| *L. plantarum* ATCC | 7 × 20 | 144 | None |
| *L. plantarum* feral | 7 × 20 | 144 | None |
| *P. aeruginosa* | 6 × 20 | 72 | None |
| *E. coli* | 6 × 20 | 72 | None |

EXAMPLE 5

Arousal Using Dilution to Affect Downshifting

Dormant cultures of *L. monocytogenes* were diluted serially 1:5 with PBS and their arousal determined after varying adjustment periods initiated after the final dilution.

TABLE 27

*L. monocytogenes* arousal by 1:5 serial dilutions in PBS, pH 7.3.

| Serial dilutions | Periods of adjustment (hrs) required for growth on: | | |
|---|---|---|---|
|  | BHI | 60 IU Amp | 30 μg TC |
| 1:5 | ND | ND | ND |
| 1:25 | 96 | ND | ND |
| 1:125 | 96 | 144 | ND |
| 1:10 | 96 | 144 | 144 |

TABLE 27-continued

L. monocytogenes arousal by 1:5 serial dilutions in PBS, pH 7.3.

| Serial dilutions | Periods of adjustment (hrs) required for growth on: | | |
|---|---|---|---|
| | BHI | 60 IU Amp | 30 μg TC |
| 1:100 | 96 | 144 | 144 |
| 1:1000 | 96 | 144 | 144 |

EXAMPLE 6

Arousal Using Dialysis to Affect Downshifting

An aliqout of culture was dialyzed against 250 volumes of PBS, pH 7.3 at 37° C. with stirring for 40 min. After an adjustment period of 18 hrs., the retentate was diluted serially 1:5 in PBS, pH 7.3, and streaked on agar.

TABLE 28

Dialysis plus dilution after 18 hrs. adjustment period for L. monocytogenes.

| Dilution after adjustment period | Growth on BHI | Growth in presence of 60 IU Amp/mL (CFUs/mL) | Growth in presence of 30 μg TC/mL (CFUs/mL) |
|---|---|---|---|
| no adjustment period and no dilution | ND | ND | ND |
| None | $10^3$ | $10^3$ | $10^3$ |
| 1:5 | $10^3$ | $10^4$ | $10^4$ |
| 1:25 | $10^5$ | $10^5$ | $10^5$ |
| 1:125 | $10^5$ | $10^5$ | $10^5$ |

TABLE 29

Dialysis plus dilution after 18 hrs. adjustment period for L. caseii.

| Dilution after adjustment period | Growth (CFUs/mL) | Growth in presence of 60 IU Amp/mL or 30 μg TC/mL (CFUs/mL) |
|---|---|---|
| None | 0 | 0 |
| 1:5 | 0 | 0 |
| 1:25 | $10^3$ * | 0 |
| 1:125 | 0 | 0 |

* = growth appeared after an grow-out period of 124 hrs. at 37° C.

Without an adjustment period of overnight (approximately 18 hrs.), dormant L. monocytogenes were not aroused. After dialysis at pH 8.0 and serial dilutions, fewer than 0.001% of the dormant cells were aroused compared to those aroused after dialysis at pH 7.3. No aroused cells were detected after dialysis at pH 6.1.

When L. caseii ATCC 393 was dialyzed against pH 7.3 as previously described, 7.5×10⁴ cells were aroused from a dormant culture, but only after an adjustment period of 124 hours at 37° C. following the dilutions of 1:5 and 1:5. They were not tolerant to ampicillin or tetracycline.

When L. plantarum ATCC 14917 was dialyzed against pH 7.3 as previously described, the culture was not aroused. However, dialyzing against four changes of 250 volumes of PBS at 37° C., at 5 and 18 hour intervals (for a total of 44 hrs. of dialysis) with no adjustment period, the retentate grew on MRS, but was not tolerant to ampicillin or tetracycline. Dialysis against 1000 volumes for 48 hours did not arouse the culture.

TABLE 30

| Culture | Dialysis | Adjustment Period (hrs.) | |
|---|---|---|---|
| | | For arousal | For hypermutation |
| L. monocytogenes | 40 min. | 24 hrs. | 24 hrs. |
| L. caseii | 40 min. | 144 hrs. + dilutions | No growth |
| L. plantarum | 4 changes in 48 hrs. | none | No growth |

EXAMPLE 7

Arousal by pH Adjustment

A dormant culture of L. monocytogenes was titrated with 10 M NaOH until the pH changed to 8 (a 1% dilution). After an adjustment period of 5 days, $10^4$ cells were aroused.

Numerous modifications or alterations may be made by one of ordinary skill in the art without departing from the spirit and scope of the invention as set forth in the claims. Accordingly, it should be understood that the foregoing description is illustrative and not intended as limiting on the scope of the invention.

What is claimed is:

1. A method for arousing dormant bacteria comprising:
   inducing diffusion of intracellular solutes from the bacteria by exposing the bacteria to a hypotonic solution via extraction, and
   allowing the bacteria to adjust to the hypotonic solution for a length of time effective to initiate arousal in the bacteria;
   said extraction comprising the steps of:
   a) microfuging the bacteria to form a pellet;
   b) suspending the pellet in a phosphate buffered saline;
   c) allowing the pellet to adjust to the saline;
   d) microfuging the pellet to form a second pellet;
   e) suspending the second pellet in phosphate buffered saline;
   f) allowing the second pellet to adjust to the saline; and
   g) repeating steps a)–c) until the method is effective in arousing the bacteria;
   said bacteria being selected from the group consisting of L. monocytogenes, L. caseii, L. plantarum, E. coli, and P. aeruginosa.

2. A method for arousing dormant bacteria comprising:
   inducing diffusion of intracellular solutes from the bacteria by exposing the bacteria to a hypotonic solution via dilution, and
   allowing the bacteria to adjust to the hypotonic solution for a length of time effective to initiate arousal in the bacteria;
   said dilution comprising the steps of:
   a) diluting the bacteria 1:5 with a phosphate buffered saline;
   b) allowing the bacteria to adjust to the saline;
   c) diluting 1:5 the initial 1:5 dilution with a phosphate buffered saline to form a 1:25 dilution; and
   d) diluting 1:5 the 1:25 dilution with a phosphate buffered saline to form a 1:125 dilution;

said bacteria being selected from the group consisting of *L. monocytogenes, L. caseii, L. plantarum, E. coli*, and *P. aeruginosa*.

3. A method for arousing dormant bacteria comprising:

inducing diffusion of intracellular solutes from the bacteria by exposing the bacteria to a hypotonic solution via dialysis, and allowing the bacteria to adjust to the hypotonic solution for a length of time effective to initiate arousal in the bacteria;

said dialysis comprising the steps of:
  a) placing the bacteria in a dialysis bag with a cutoff of about 10 kDa;
  b) dialysing the bacteria against 250 volumes of phosphate buffered saline to form a retentate and a diffusate;
  c) removing the retentate;
  d) allowing the retentate to adjust to the saline; and
  e) diluting the adjusted retentate 1:5 with phosphate buffered saline twice;

said bacteria being selected from the group consisting of *L. monocytogenes, L. caseii, L. plantarum, E. coli*, and *P. aeruginosa*.

* * * * *